United States Patent [19]
Ben-Hur et al.

[11] Patent Number: 5,637,451
[45] Date of Patent: Jun. 10, 1997

[54] PHOTODYNAMIC TREATMENT OF RED BLOOD CELLS WITH PHTHALOCYANINES AND RED LIGHT AT HIGHER LIGHT FLUENCE RATES IS PROTECTIVE OF RED BLOOD CELLS

[75] Inventors: Ehud Ben-Hur, New York; Bernard Horowitz, New Rochelle, both of N.Y.

[73] Assignee: New York Blood Center, Inc., New York, N.Y.

[21] Appl. No.: 413,054

[22] Filed: Mar. 29, 1995

[51] Int. Cl.$^6$ ............... A01N 1/02; A01N 63/00; C12N 7/06
[52] U.S. Cl. ............... 435/2; 435/238; 424/93.73
[58] Field of Search ............... 435/2, 238; 424/93.73

[56] References Cited

U.S. PATENT DOCUMENTS 5,120,649  6/1992  Horowitz et al. ............... 435/173
5,232,844  8/1993  Horowitz et al. ............... 435/173.1

OTHER PUBLICATIONS

Ben–Hur E et al, 22nd Annual Meeting of The Am. Soc. for Photobiology in Photochem & Photobiol. 59: 74S–75S (1994).
Ben–Hur E et al, Cancer Lett 30: 321–27 (1986).

*Primary Examiner*—Michael G. Wityshyn
*Assistant Examiner*—Sandra Saucier
*Attorney, Agent, or Firm*—Sprung Horn Kramer & Woods

[57] ABSTRACT

An improved process for inactivating an extracellular lipid enveloped virus or an intracellular lipid enveloped virus which may be present in an extracorporeal composition containing red blood cells by subjecting the composition to a virucidally effective amount of a phthalocyanine compound and red light of a fluence rate of at least above about 5 mW/cm$^2$. Quite contrary to what would have been expected, it has been found that higher light fluence rates are, in fact, more protective of red blood cells than are lower light fluence rates.

7 Claims, 6 Drawing Sheets

PHOTODYNAMIC TREATMENT OF RED BLOOD CELLS WITH PHTHALOCYANINES AND RED LIGHT AT HIGHER LIGHT FLUENCE RATES IS PROTECTIVE OF RED BLOOD CELLS

GOVERNMENT RIGHTS

This invention was made with government support under 1-R01-HL41221 awarded by the National Institutes of Health. The government has certain rights in this invention.

BACKGROUND OF THE INVENTION

1. Field of the Invention

The present invention relates to an improved process for inactivating a virus which may be present in blood or blood products by treating the blood or blood product with a phthalocyanine dye under the influence of red light.

2. Description of the Related Art

Despite impressive reduction during the last decade in the risk of human pathogenic viruses as a result of blood transfusion, complete viral safety has not been achieved (R. Y. Dodd, "The risk of transfusion-transmitted infection", *N. Eng. J. Med.*, 327, 419–421, 1992). Most of these viruses are lipid enveloped and their inactivation in cellular components of blood is the subject of intensive research.

Photochemical methods are the most promising for virus sterilization of platelets and red blood cells (RBC). For decontamination of platelet concentrates, UVA light and psoralens (PUVA) has been shown to be highly effective (L. Lin et al., "Use of 8-methoxypsoralen and long wavelength ultraviolet radiation for decontamination of platelet concentrates", *Blood*, 74, 517–525, 1989; R. Y. Dodd et al., "Inactivation of viruses in platelet suspensions that retain their in vitro characteristics: comparison of psoralen-ultraviolet A and merocyanine 540-visible light methods", *Transfusion*, 31, 483–490, 1991; and H. Margolis-Nunno et al., "Virus sterilization in platelet concentrates with psoralen and ultraviolet A light in the presence of quenchers", *Transfusion*, 32, 541–547, 1992).

For viral inactivation in RBC suspensions, red light ($\lambda > 600$ nm) has to be used to avoid light absorption by hemoglobin. Following the pioneering work by Matthews et al. ("Photodynamic therapy of viral contaminants with the potential for blood banking applications", *Transfusion*, 28, 81–83, 1988) using HPD, other sensitizers with strong absorption in the far red have been employed (H. C. Neyndorff et al., "Development of a model to demonstrate photosensitizer mediated viral inactivation in blood", *Transfusion*, 30, 485–490, 1990; and M. M. Judy et al., "In vitro photodynamic inactivation of herpes simplex virus with sapphryins: $22\pi$-electron porphyrin-like macrocycles", *Photochem. Photobiol.*, 53, 101–107, 1991).

Our laboratory has focused on the phthalocyanines as sensitizers for inactivation of lipid enveloped viruses (B. Horowitz et al., "Inactivation of viruses in blood with aluminum phthalocyanine derivatives", *Transfusion*, 31, 102–108, 1991; and E. Ben-Hur et al., "Photodynamic inactivation of retroviruses by phthalocyanines: the effect of sulfonation, metal ligand and fluoride", *J. Photochem. Photobiol. B. Biol.*, 13, 145–152, 1992). To obtain maximum virucidal action while minimizing damage to RBC we have used two approaches. One was to screen for structural features of phthalocyanines that enhance viral inactivation and reduce RBC damage (E. Ben-Hur et al., "Phthalocyanine-induced photohemolysis: structure activity relationship and the effect of fluoride", *Photochem. Photobiol.*, 58, 351–355, 1993; Z. Smetana et al., "Photodynamic inactivation of herpes viruses with phthalocyanine derivatives" *J. Photochem. Photobiol. B. Biol.*, 22, 37–43, 1994; and S. Rywkin et al., "New phthalocyanines for photodynamic virus inactivation in red blood cell concentrates", *Photochem. Photobiol.*, 60, 165–170, 1994). The second approach was to use scavengers of reactive oxygen species. It appears that quenchers of type I photodynamic reactions can reduce RBC damage without reducing virus inactivation (S. Rywkin et al., "Importance of type I and type II mechanisms in the photodynamic inactivation in blood with aluminum phthalocyanine derivatives", *Photochem. Photobiol.*, 56, 463–469, 1992). This is presumably due to singlet oxygen being the primary mediator of virus killing while both types I and II reactions contribute to RBC damage. See also our earlier U.S. Pat. Nos. 5,120,649 and 5,232,844 and copending application Ser. Nos. 08/031,787, 08/344,919 and 08/364,031, the entire disclosures of which patents and applications are hereby incorporated by reference.

In spite of these advances, there remains a definite need in the art for new methods or improvements in existing methods which cause less RBC damage without also reducing virus kill.

SUMMARY OF THE INVENTION

Accordingly, it was the principal object of the present invention to provide an improved blood sterilization procedure whereby extracellular or intracellular lipid enveloped virus which may be present in blood or blood products are substantially inactivated under conditions wherein little or no damage is done to blood cells, especially RBC, and labile biological proteins contained in such blood or blood products.

Toward this end, we investigated a third possible approach to enhance the selectivity of virus inactivation in blood, i.e., a change in the light fluence rate. Cells are able to deal with reactive oxygen species by various mechanisms such as quenchers and antioxidant enzymes (G. R. Buettner, "The pecking order of free radicals and antioxidants: lipid peroxidation, $\alpha$-tocopherol and ascorbate", *Arch. Biochem. Biophys.*, 300, 535–543. 1993; and P. Cerutti et al., "Oxy-radicals in Molecular Biology and Pathology", Alan R. Liss, New York, 1988). Therefore, it would have been expected that when photodynamic treatment is delivered at a reduced fluence rate, the blood cells would be able to tolerate the treatment better. This has been shown for mammalian cells (fibroblasts derived from Chinese hamsters) photosensitized with $AlPcS_n$ (E. Ben-Hur et al., "Effect of light fluence rate on mammalian cells photosensitization by aluminum phthalocyanine tetrasulfonate", *Int. J. Radiat. Biol.*, 51, 467–476, 1987) and HPD (W. Matthews et al., "In vitro photodynamic therapy of human lung cancer: Investigation of dose-rate effects", *Cancer Res.*, 49, 1718–1721, 1989). Since viruses are devoid of such protective mechanisms, their inactivation rate is not expected to be affected by the light fluence rate. Thus, by modulating the rate at which the light is delivered, treatment conditions can be optimized in virus RBC sterilization protocols.

However, in contrast to these expectations, we have discovered that surprisingly, using phthalocyanines as sensitizers, the extent of RBC damage actually decreased with increasing fluence rate.

Therefore, the present invention relates to an improved process for inactivating an extracellular lipid enveloped virus or an intracellular lipid enveloped virus which may be present in an extracorporeal composition containing red blood cells, said process comprising subjecting said composition to a virucidally effective amount of a phthalocyanine compound and red light, wherein the improvement comprises subjecting said composition to a virucidally effective amount of a phthalocyanine compound and red light of a fluence rate of at least above about 5 mW/cm$^2$.

BRIEF DESCRIPTION OF THE DRAWINGS

The invention will now be described in greater detail with reference to the drawings, wherein.

DETAILED DESCRIPTION OF THE INVENTION

Figure 1:
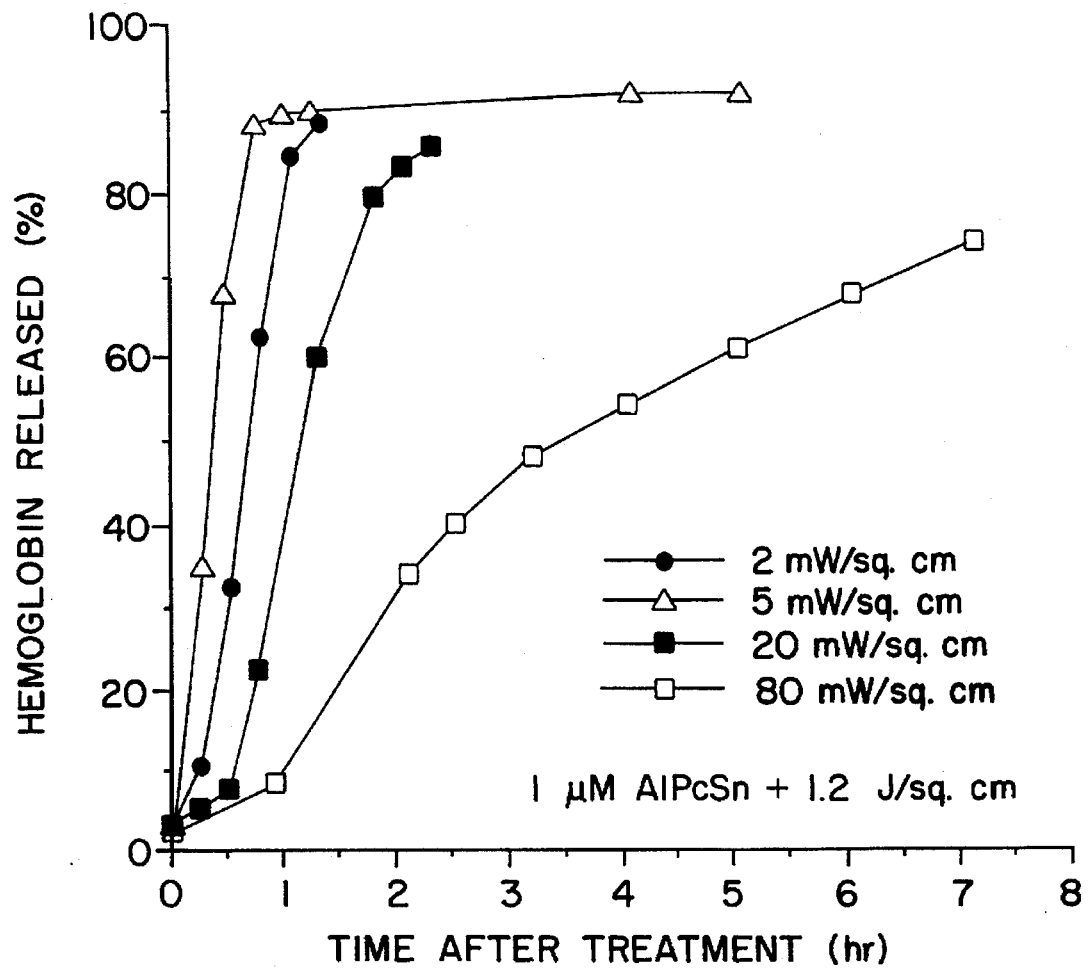
FIG. 1 is a graph showing the hemolytic curves of RBC following exposure to 1.2 J/cm$^2$ at various fluence rates, in the presence of 1 μM AlPcS$_n$.

Conditions for photodynamic treatment of red blood cell containing compositions using phthalocyanines and red light are described in detail in the aforementioned patents and applications.

The extracorporeal composition containing red blood cells is preferably selected from the group consisting of whole blood and red cell concentrates.

According to the teachings of the present invention, superior viral inactivation and retention of red cell structure and function is retained by subjecting the extracorporeal composition containing red cells to red light of a fluence rate of at least about 5 mW/cm$^2$. Preferably, the red light fluence rate is greater than at least about 20 mW/cm$^2$. Most preferably, the red light fluence rate is about 20 mW/cm$^2$ to about 80 mW/cm$^2$, but 80 mW/cm$^2$ is the maximum fluence rate obtainable with our light source. It is likely that higher fluence rates will yield even better results. The wavelength of this light is greater than 600 nm, preferably greater than 650 nm and, most preferably, between about 660 to 690 nm.

In general, the extracorporeal composition containing red cells is subjected to red light for a period of time ranging from 5 minutes to 5 hours. Preferably, the time period ranges from 5 minutes to 1 hour, most preferably, from 5 minutes to 20 minutes. Of course, the total fluence (J/cm$^2$) is calculated by multiplying the fluence rate (mW/cm$^2$=J/cm$^2$/sec) by the time of irradiation (in seconds).

In the inventive methods, various phthalocyanine dyes, many of which are already known in the art, may be used. Non-limiting examples of phthalocyanines for use in the present invention include:

zinc tetrasulfophthalocyanine;
tetrasulfophthalocyanine;
aluminum tetranitrophthalocyanine;
zinc tetranitrophthalocyanine;
tetracarboxyphthalocyanine;
GaCl-tetrasulfophthalocyanine;
AlCl-tetrasulfophthalocyanine;
Ga-tetrasulfophthalocyanine; and
GaCl-, AlCl- or Ga-tetranitrophthalocyanine.

A preferred embodiment of the present invention involves the use of cationic phthalocyanine Pc 5 (HOSiPcOSi(CH$_3$)$_2$(CH$_2$)$_3$N+(CH$_3$)$_3$I—) and its neutral analog Pc 4 (HOSiPcOSi(CH$_3$)$_2$(CH$_2$)$_3$N(CH$_3$)$_2$). Also preferred is the use of phthalocyanines of the formula AlPcS$_n$, wherein n is 3 or 4. The dyes are added to the extracorporeal red blood cell composition to a concentration of the dye of up to 10 μM. Preferred concentrations for the dyes are 1 to 5 μM, most preferably about 2 μM.

When quenchers are employed, any quencher compounds that scavenge free radicals or reactive oxygen species, such as singlet oxygen, may be used alone or in combination. Types of quenchers, quencher combinations and suitable amounts contemplated are set forth in detail in the aforementioned patents and applications, but preference is given to mannitol, glutathione (GSH), vitamin E and derivatives thereof such as Trolox. Preferred are the use of quencher combinations calculated to quench both free radical or singlet oxygen generating reactions or of individual quencher compounds capable of quenching both types of reactions.

Examples of viruses that can be inactivated by the inventive method are hepatitis B virus (HBV), non-A, non-B hepatitis virus (NANBHV), e.g., hepatitis C virus (HCV), and human immunodeficiency virus (HIV). However, for a more detailed list of such viruses, please see the aforementioned patents and applications.

The inventive method is protective of blood cells, especially red blood cells, and labile blood proteins. In general, red cells and platelets retain at least 70% and, preferably, greater than 80% and, more preferably, greater than 95% of structural integrity. Structural integrity of red cells is measured by counting the number of red cells remaining after the photodynamic treatment or by assaying the amount of hemoglobin released as a result of said treatment. For example, if at least 70% of said red cells remain after said treatment or if less than 30% of the initial hemoglobin is released after said treatment, then a structural integrity of at least 70% of said red cells has been retained. Similarly, structural integrity of platelets is determined by counting the number of platelets remaining after said treatment or by determining the aggregation of the platelets as compared to an untreated control upon the addition of a biological aggregation agent, for example, collagen. In the case of labile biological proteins, a recovery of at least 70% and, preferably, greater than 80% and, more preferably, greater than 95% is achieved. Methods for assaying labile blood protein activity and other methods for assaying structural and functional integrity of blood cells are discussed in the aforementioned patents and applications.

The invention will now be described in the following non-limiting example.

EXAMPLE

Materials and Methods

RBC: Whole blood, obtained from the New York Blood Center, was centrifuged at 1800 rpm for 20 min and the plasma and white blood cells were removed. The RBC concentrate (70% hematocrit) was diluted 1:1 with phosphate buffered saline (PBS) and either irradiated at 35% hematocrit or further diluted and irradiated at a concentration of $5 \times 10^7$ cells/ml.

Light exposure: The light source used was a 500 W Xenon short arc lamp (Versa Light, Medic Lightech Ltd., Haifa, Israel) equipped with filters transmitting red light at 600 nm<λ<700 nm. The light was delivered via 1.5 m flexible fiber optic bundle terminated with a lens. The light fluence rate incident onto the sample was measured with a photometer (Model 1L 1350, International Light, Newburyport, Mass.) and was adjusted by varying the sample distance and power supply. Samples of 3 ml RBC suspensions were irradiated in 5 cm petri dishes without covers and stirred with a magnetic bar. Temperature during irradiation was 24°±1° C. Phthalocyanines were added to RBC 30 min prior to light exposure.

Phthalocyanines: AlPCS$_n$ (a mixture of tri- and tetrasulfonated aluminum phthalocyanine) was kindly supplied by Ciba-Geigy, Basel. A stock solution of 1 mM was prepared in PBS and stored at 4° C. prior to use. Pc 5 was prepared as described previously (N. L. Olenick et al., "New phthalocyanine photosensitizers for photodynamic therapy", *Photochem. Photobiol.*, 57, 242–247, 1993) and a 1 mM stock solution DMSO was stored at −20° C.

VSV assay: Assay of vesicular stomatis virus (VSV) was done as described previously (B. Horowitz et al., "Inactivation of viruses in blood with aluminum phthalocyanine derivatives", *Transfusion*, 31, 102–108, 1991). Briefly, VSV was added into RBC (35% hematocrit) to a final titer of $10^6$ infectious units per ml. After 30 min dark incubation together with Pc the samples were irradiated and the suspension diluted 1:10 with Dulbecco's modified Eagle's medium (DMEM) containing 5% fetal calf serum (FCS) and centrifuged to remove RBC. The supernatants were sterile filtered by passing through 0.22µ filters (Millipore) and stored frozen at −80° C. For assay the samples were 10-fold serially diluted, inoculated into A549 cell cultures in 96-well microtiter plates and incubated for 72 h. The cytopathology of the cells was then scored in eight well replicates for each dilution. Quantitation of the virus titer was done with the Spearman-Karber method (C. Spearman, "The method of right and wrong cases (constant stimuli) with Gauss formulae", *Br. J. Psychol.*, 2, 227–242, 1908).

RBC hemolysis: RBC suspensions at $5 \times 10^7$ cells/ml in PBS were irradiated and then incubated in the dark at 24° C. At intervals 0.3 mL cell suspension was added to 3 ml PBS and mixed. The cells were centrifuged at 4° C. for 5 min, and the hemoglobin content of the supernatant was measured by recording absorbance at 415 nm. Percentage hemolysis was then calculated (100% was taken as the absorbance obtained in a sample lysed in distilled water). The time required to obtain 50% hemolysis is designated $t_{50}$, and its reciprocal was used to estimate the rate of photohemolysis. Each experiment was repeated 2–3 times with essentially the same results. In experiments involving D$_2$O (99.9 atom % D, from Aldrich), the cells were suspended in PBS-D$_2$O during irradiation only. For light exposure under O$_2$ atmosphere, O$_2$ (99.9%) was bubbled through the cell suspension 1 min prior to and during irradiation.

RBC binding to PLL. The reduction of RBC surface negative charges as a result of photosensitization was assayed by measuring RBC binding to poly-L-lysine (PLL) (S. Rywkin et al., "New phthalocyanines for photodynamic virus inactivation in red blood cell concentrates", *Photochem. Photobiol.*, 60, 165–170, 1994). Briefly, RBC at 35% hematocrit were irradiated and diluted in PBS to a concentration of $5 \times 10^6$ cells/mL. One mL of cell suspension was added into 35 mm Petri dish pre-coated with PLL and incubated at room temperature for 1 hr. The plates were then rinsed with PBS and the adsorbed cells were lysed with 2 ml distilled water. The absorbance at 415 nm of the lysate was used to quantitate the hemoglobin released from the adherent RBC, and the results calculated as a percentage of those obtained from untreated controls. Standard errors were less than 10% and are not shown for clarity.

Results

Figure 2:
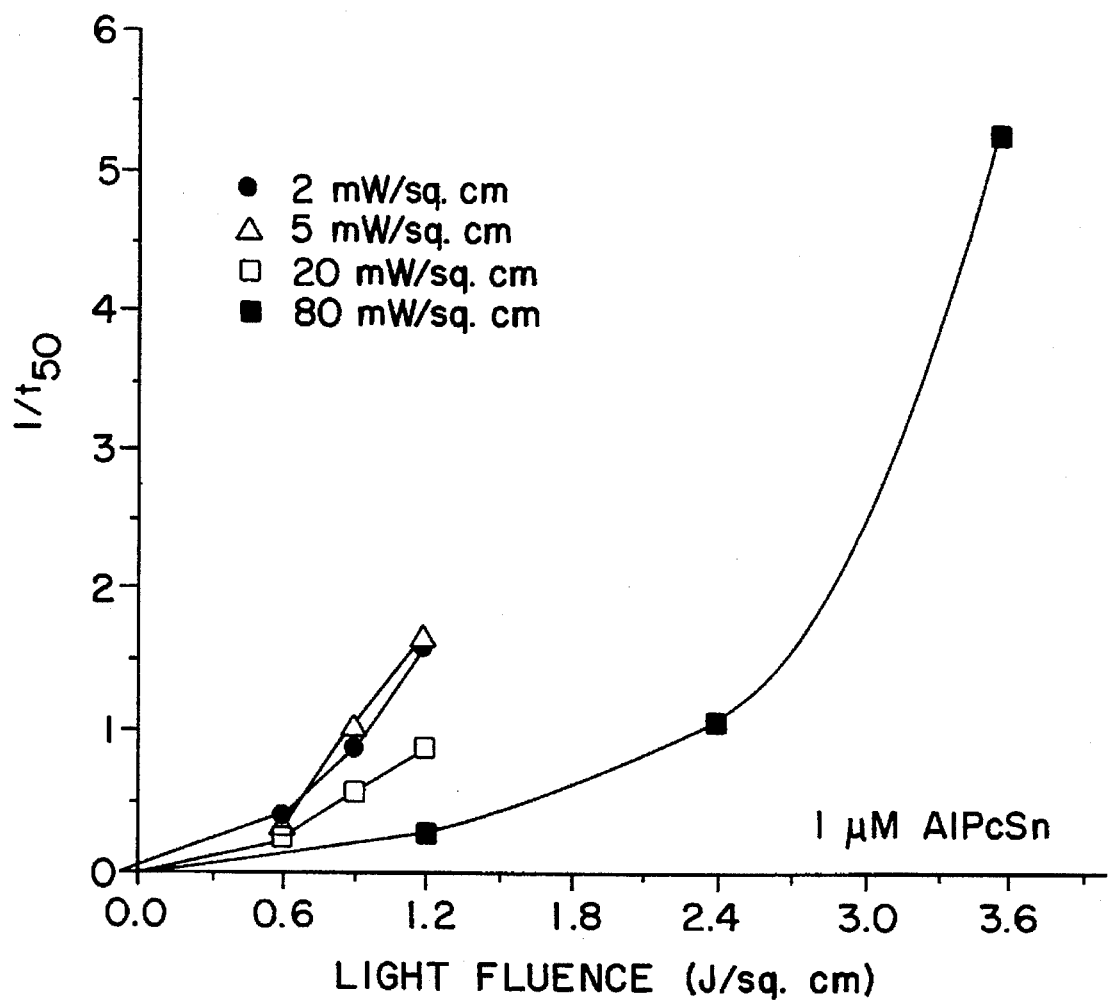
FIG. 2 is a graph showing the rate of hemolysis (1/t$_{50}$) as a function of light fluence rate for treatment with AlPcS$_n$.
Figure 3:
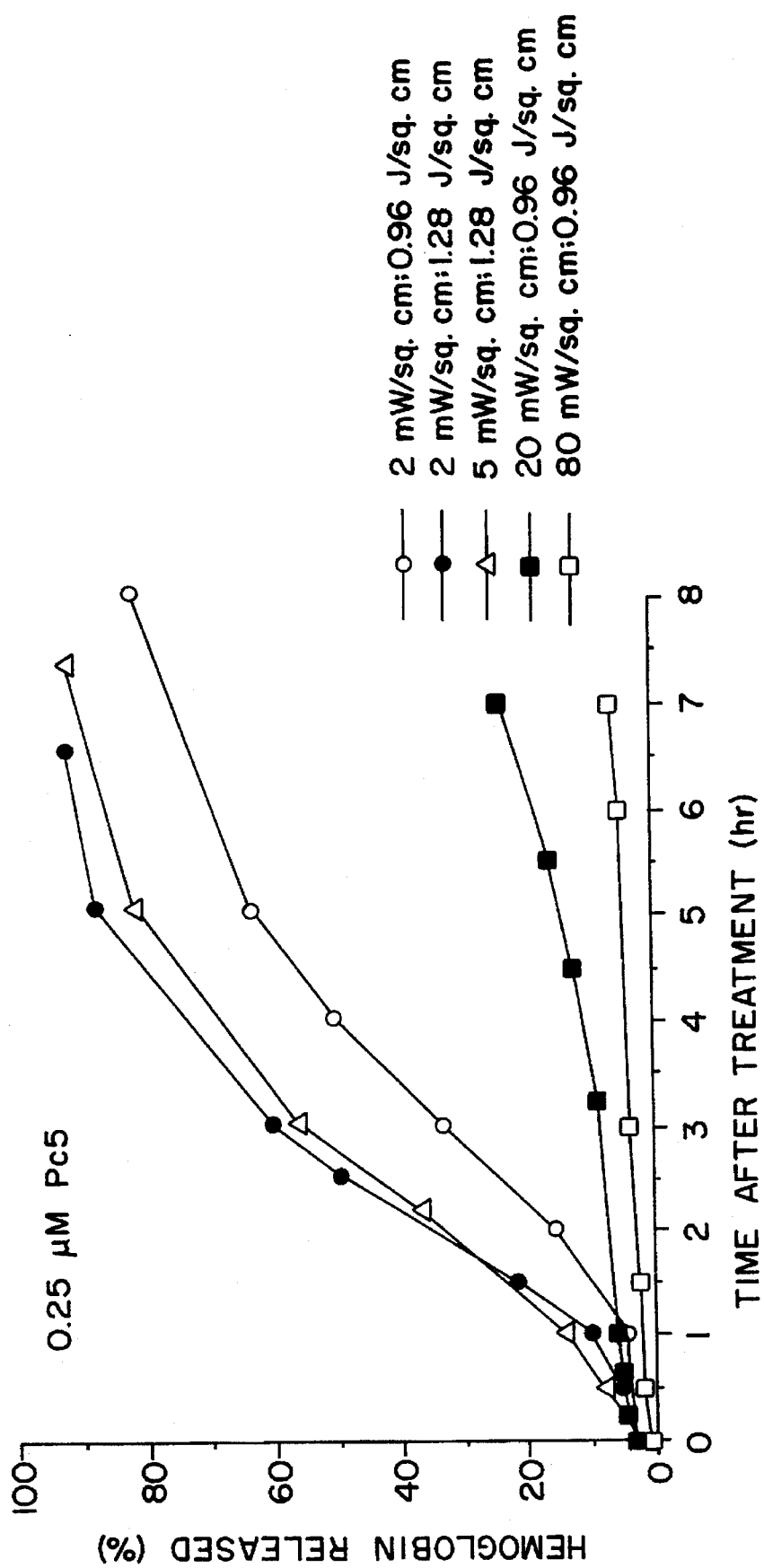
FIG. 3 is a graph showing the hemolytic curves of RBC following exposure to 0.96 and 1.28 J/cm$^2$ as a function of light fluence rate for treatment with 0.25 μM Pc 5.
Figure 4:
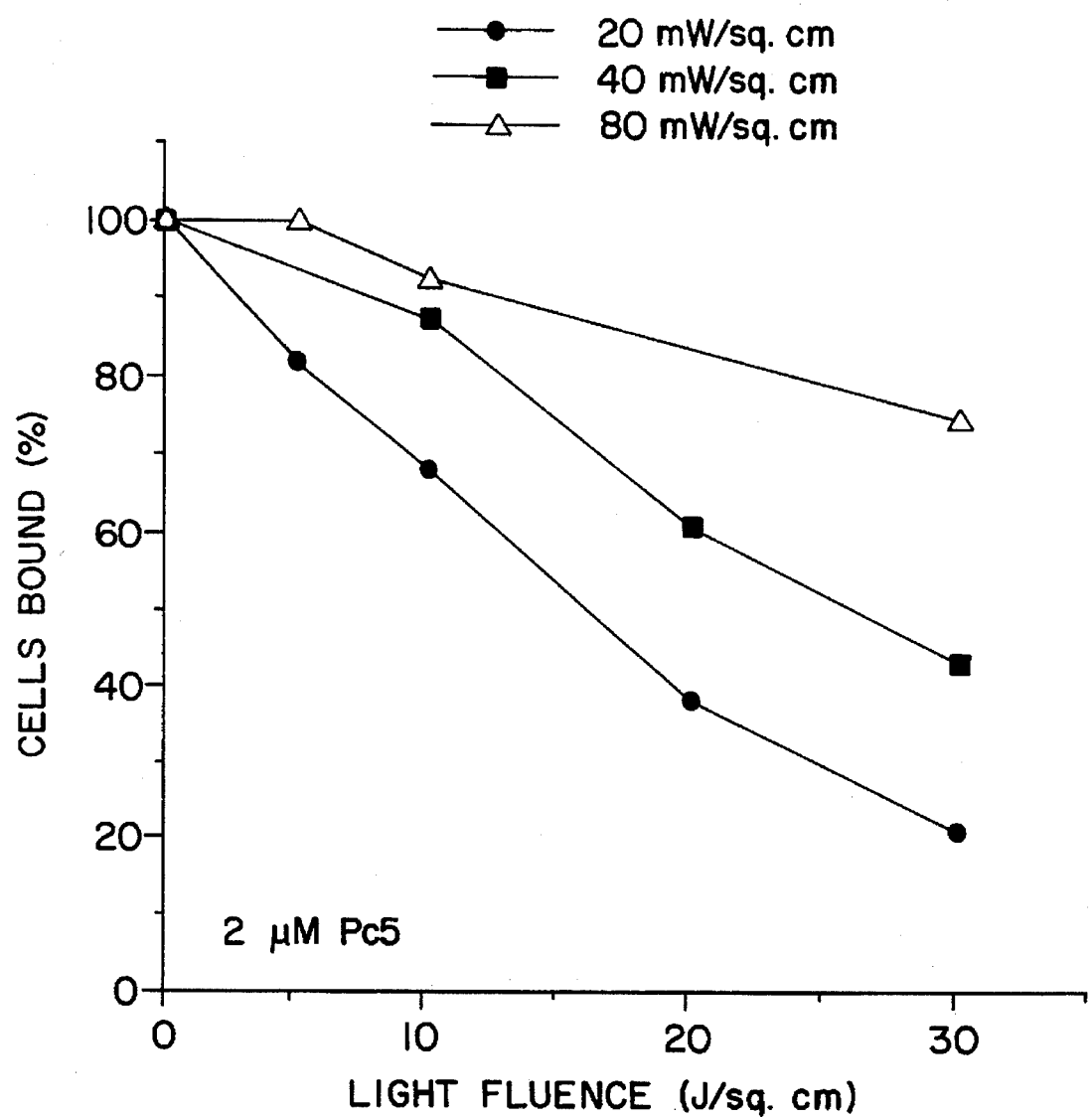
FIG. 4 is a graph showing the fluence rate response curves for reduction of RBC binding to PLL sensitized by 2 μM Pc 5 at various fluence rates.
Figure 5:
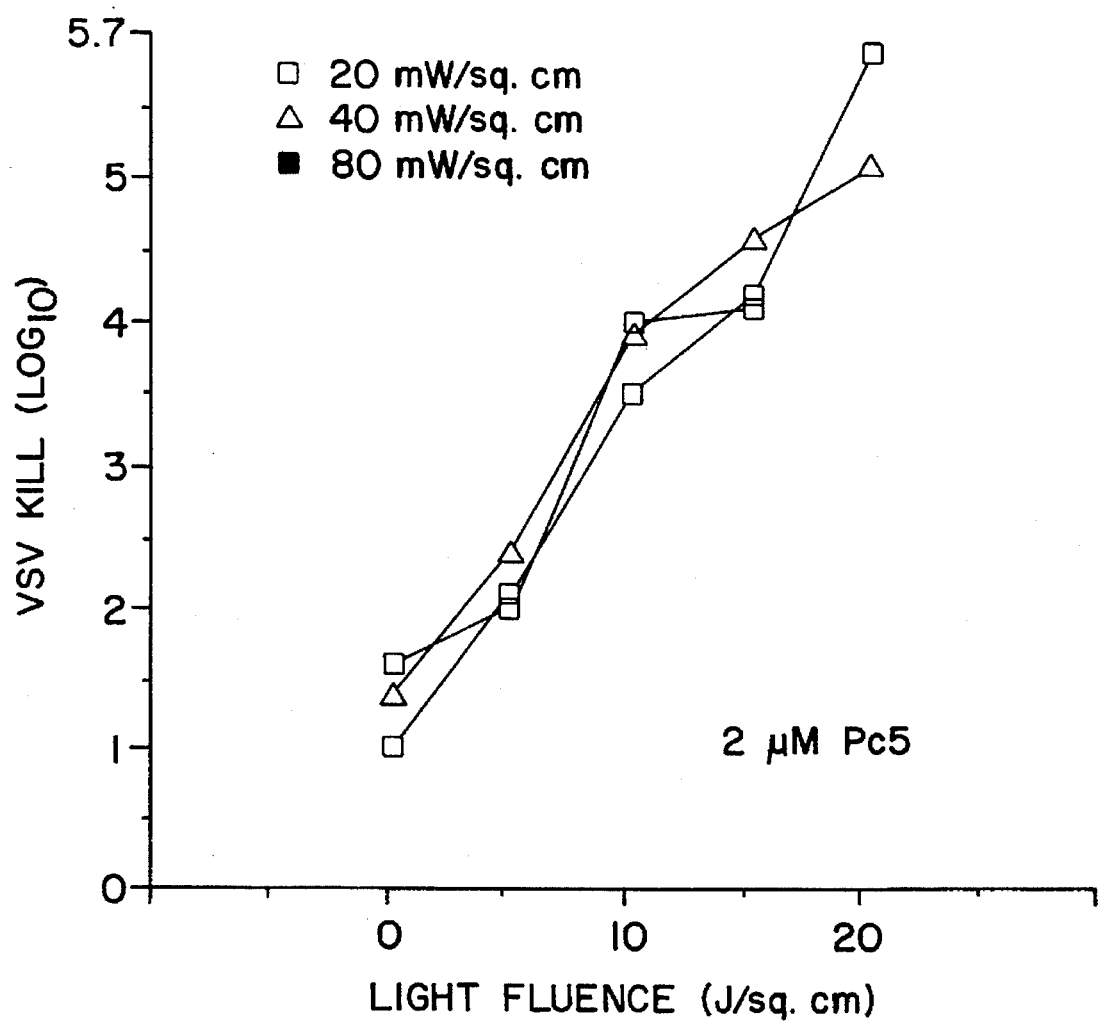
FIG. 5 is a graph showing VSV inactivation sensitized by 2 μM Pc 5 at various fluence rates.

FIG. 1 shows the hemolytic curves of RBC following exposure to 1.2 J/cm$^2$ at various fluence rates, in the presence of 1 µM AlPcS$_n$. It can be seen that as the fluence rate increased between 5 and 80 mW/cm$^2$, hemolysis became slower. A more quantitative analysis is shown in FIG. 2, where the rate of hemolysis ($1/t_{50}$) was plotted as a function of light fluence rate. Again, at fluence rates above 5 mW/cm$^2$ there was an inverse relationship between the rate of hemolysis and the fluence rate. To test the generality of this phenomenon with other phthalocyanines we used Pc 5, a more potent virucidal sensitizer than AlPcS$_n$ (S. Rywkin et al., "New phthalocyanines for photodynamic virus inactivation in red blood cell concentrates", *Photochem. Photobiol.*, 60, 165–170, 1994). Because Pc 5 is also more effective in causing RBC damage, a lower sensitizer concentration was used. The results show that with Pc 5 the same inverse relationship occurs between fluence rate (above 5 mW/cm$^2$) and the rate of hemolysis (FIG. 3). Under our standard virucidal treatment conditions (35% hemocrit) hemolysis is minimal and cannot be used as a useful assay to quantitate RBC damage (B. Horowitz et al., "Inactivation of viruses in blood with aluminum phthalocyanine derivatives", *Transfusion*, 31, 102–108, 1991; and S. Rywkin et al., "New phthalocyanines for photodynamic virus inactivation in red blood cell concentrates", *Photochem. Photobiol.*, 60, 165–170, 1994). We therefore measured reduction in RBC negative surface charges as an endpoint. FIG. 4 shows that under these conditions RBC damage again was reduced as the fluence rate increased between 20 and 80 mW/cm$^2$, using Pc 5 as a photosensitizer. When RBC were spiked with VSV, complete viral kill occurred after 20 J/cm$^2$ (FIG. 5), independent of the fluence rate.

Figure 6:
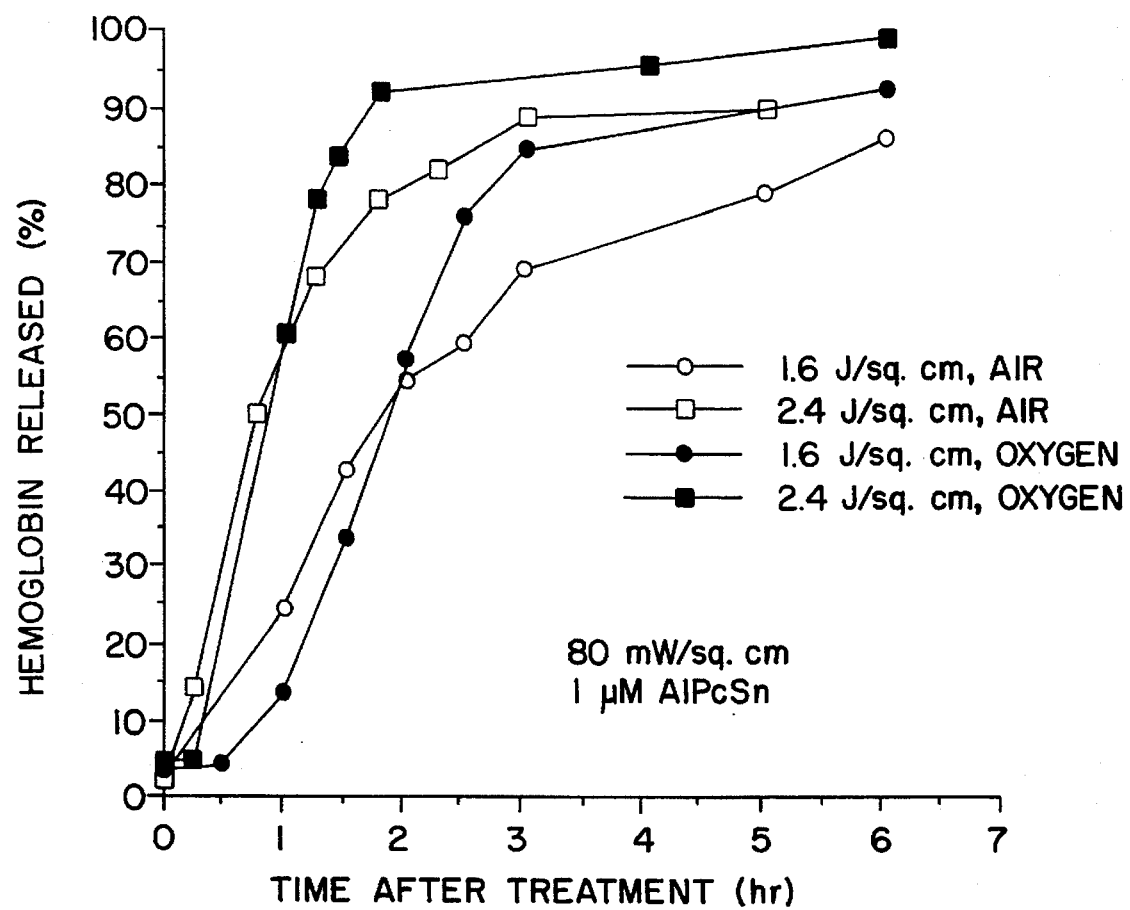
FIG. 6 is a graph showing the photohemolysis of RBC sensitized by 1 μM AlPcS$_n$ at 80 mW/cm$^2$, exposed to 1.6 and 2.4 J/cm$^2$ under air or oxygen atmosphere.

A possible explanation for the effect of the fluence rate is depletion of oxygen from the cell suspension during light exposure at high fluence rates. To test this possibility we compared photohemolysis at 80 mW/cm$^2$ saturated with air or with oxygen (1 atmosphere pressure). The results obtained at two different light fluences show no significant dependence on oxygen concentration (FIG. 6).

Contrary to our expectation, RBC damage produced upon photosensitization with phthalocyanines was inversely related to light fluence rate between 5 and 80 mW/cm$^2$. The most trivial explanation for this is that oxygen becomes rate limiting for the photodynamic reactions at high fluence rates. This possibility has been ruled out because the effect was not reduced when exposure was carried out in oxygen-saturated rather than air-saturated solutions (FIG. 6). This is also consistent with a lack of a fluence rate effect on VSV inactivation, which would be difficult to explain if depletion of oxygen played a role in this effect.

Other possible explanations for the fluence rate effect can be invoked and are based on an enhancement of the quenching of reactive species at high fluence rates. For example, $^1O_2$ can form dimoles, $(^1O_2)_2$, the concentration of which should be proportional to the square of the light fluence rate.

Tetra-t-butylphthalocyanine is particularly effective in sensitizing dimol $^1O_2$ in organic solvents (A. A. Krasnovsky et al., "Time-resolved measurements of singlet-oxygen dimol-sensitized luminescence", *J. Am. Chem. Soc.*, 115, 6013–6016, 1993). To test whether dimol production is responsible for the observed effect, the experiment shown in FIG. 1 was performed in $D_2O$. Although $D_2O$ enhances photohemolysis under these conditions (I. Rosenthal et al., "Ascorbate-assisted, phthalocyanine-sensitized photohaemolysis of human erythrocytes", *Int. J. Radiat. Biol.*, 62, 481–486, 1992), suggesting the involvement of $^1O_2$, the fluence rate effect was not affected (data not shown). These results argue against dimol contribution to the basic observations.

Another possibility is the quenching of $^1O_2$ by sensitizer molecules in their triplet excited states (R. D. Kenner et al., "Singlet molecular oxygen annihilation luminescence in polymers", *J. Chem. Phys.*, 64, 1877–1882, 1977). Basically, if energetic requirements are met, the $^1O_2$ can collide with an aromatic photosensitizer molecule (P) in its triplet excited state, thus generating the singlet excited state of P. The net result is that a biphotonic mechanism leads to the deactivation of a $^1O_2$ molecule. This mechanism depends on the absorption of two photons: the first photon generates the $^3P$ sensitizer that produces the $^1O_2$ molecule in the first place. The second photon generates another $^3P$ molecule that serves as a quencher for the $^1O_2$ resulting from the first photon absorption. Obviously, this mechanism should be characterized by a decreasing yield of $^1O_2$ molecules with increasing fluence rate. The observation of such a mechanism should by facilitated at high sensitizer concentration. However, when the experiment shown in FIG. 1 was performed at 4-fold lower concentration of $AlPcS_n$ the fluence rate effect was not affected (data not shown). This experiment also makes the possibility that recombination of other reactive oxygen species (e.g. OH radicals) underlies the fluence rate effect less likely.

Indeed, in view of the lack of a fluence rate effect for viral inactivation, it is difficult to see how any of the above could explain an effect that is specific to RBC. However, while its mechanism is presently unknown, the fluence rate effect has an obvious practical application for photochemical blood sterilization. The use of high fluence rates, especially 80 mW/cm$^2$ and above, would minimize RBC damage and allow higher light fluences to be used in the process.

It will be appreciated that the instant specification and claims are set forth by way of illustration and not limitation, and that various modifications and changes may be made without departing from the spirit and scope of the present invention.

What is claimed is:

1. In a process for inactivating an extracellular lipid enveloped virus or an intracellular lipid enveloped virus which may be present in an extracorporeal composition comprising red blood cells, said process comprising subjecting said composition to a virucidally effective amount of a phthalocyanine compound and red light of a wavelength greater than 600 nm, wherein the improvement comprises subjecting said composition to a virucidally effective amount of a phthalocyanine compound and red light of a fluence rate of at least about 40 mW/cm$^2$.

2. The process according to claim 1, wherein the red light is of a fluence rate of about 40 mW/cm$^2$ to about 80 mW/cm$^2$.

3. The process according to claim 1, wherein the red light is of a fluence rate of at least about 80 mW/cm$^2$.

4. The process according to claim 1, wherein the extracorporeal composition comprising red blood cells is selected from the group consisting of whole blood and red cell concentrates.

5. The process according to claim 1, wherein the phthalocyanine compound is selected from the group consisting of phthalocyanines of the formula $AlPcS_n$, wherein n is 3 or 4, Pc 4 and Pc 5.

6. The process according to claim 1, wherein the extracorporeal composition comprising red blood cells is subjected to a virucidally effective amount of a phthalocyanine compound and red light of a fluence rate of at least about 40 mW/cm$^2$ in the presence of a quencher compound.

7. The process according to claim 1, wherein the extracorporeal composition comprising red blood cells contains at least one virus which is inactivated and which is selected from the group consisting of hepatitis B virus (HBV), non-A, non-B hepatitis virus (NANBHV) and human immunodeficiency virus (HIV).

* * * * *